(12) United States Patent
Fenton, Jr. et al.

(10) Patent No.: US 12,029,640 B2
(45) Date of Patent: Jul. 9, 2024

(54) METHOD AND INJECTION SYSTEM FOR BONE TISSUE IMPLANT

(71) Applicants: Paul V. Fenton, Jr., Marblehead, MA (US); George A. Adaniya, Rockport, MA (US)

(72) Inventors: Paul V. Fenton, Jr., Marblehead, MA (US); George A. Adaniya, Rockport, MA (US)

(*) Notice: Subject to any disclaimer, the term of this patent is extended or adjusted under 35 U.S.C. 154(b) by 0 days.

(21) Appl. No.: 16/212,874

(22) Filed: Dec. 7, 2018

(65) Prior Publication Data

US 2019/0175329 A1 Jun. 13, 2019

Related U.S. Application Data

(60) Provisional application No. 62/595,615, filed on Dec. 7, 2017.

(51) Int. Cl.
*A61B 17/88* (2006.01)
*A61F 2/08* (2006.01)
(Continued)

(52) U.S. Cl.
CPC ........ *A61F 2/0805* (2013.01); *A61B 17/8811* (2013.01); *A61B 17/8836* (2013.01);
(Continued)

(58) Field of Classification Search
CPC ............ A61F 2/0805; A61F 2002/0817; A61F 2002/0852; A61F 2002/0888;
(Continued)

(56) References Cited

U.S. PATENT DOCUMENTS

| 4,702,236 A | 10/1987 | Tarabichy et al. |
| 4,963,151 A | 10/1990 | Ducheyne et al. |

(Continued)

FOREIGN PATENT DOCUMENTS

| EP | 2206467 | 7/2010 |
| WO | WO 96/39107 | 12/1996 |

OTHER PUBLICATIONS

Andreykiv, A. et al., On stabilization of loosened hip stems via cement injection into osteolytic cavities, Clinical Biomechanics, vol. 27, No. 8, 2012, pp. 807-812.
(Continued)

*Primary Examiner* — Brian A Dukert
*Assistant Examiner* — Melissa A Hoban
(74) *Attorney, Agent, or Firm* — Pandiscio & Pandiscio (57) ABSTRACT

An implant injection system and method for introducing a bone implant material into a patient's bone to serve as an anchor or to fill a void in the bone. The system and method provide a quantity of meltable material which is melted in situ so that the melted material can flow and diffuse into, and be anchored to, the cancellous bone portion beneath the cortical bone layer. The flowing of the bone implant material can be accomplished by a heater located at the distal end of the implant injection system. The implant material may be provided in multiple layers with an inner layer having a lower flowing temperature than the outer layers. There can also be a looped suture that passes though the meltable material, with the free ends of the suture extending outwardly to be tied to soft tissue to affix the soft tissue to the bone.

13 Claims, 7 Drawing Sheets (51) Int. Cl.
 *A61L 24/06* (2006.01)
 *A61L 27/18* (2006.01)
 *A61B 17/00* (2006.01)
(52) U.S. Cl.
 CPC .............. *A61L 24/06* (2013.01); *A61L 27/18* (2013.01); *A61B 2017/005* (2013.01); *A61B 2017/00734* (2013.01); *A61F 2002/0817* (2013.01); *A61F 2002/0852* (2013.01); *A61F 2002/0888* (2013.01); *A61F 2210/0085* (2013.01); *A61L 2400/06* (2013.01)
(58) Field of Classification Search
 CPC ......... A61F 2210/0085; A61B 17/8811; A61B 17/88; A61B 17/8805; A61B 17/8836; A61B 2017/005; A61B 2017/00734; A61L 24/06; A61L 27/18; A61L 2400/06
 See application file for complete search history.

(56) References Cited

U.S. PATENT DOCUMENTS

| | | | |
|---|---|---|---|
| 5,376,123 A | 12/1994 | Klaue et al. | |
| 5,387,243 A | 2/1995 | Devanathan | |
| 5,944,686 A | 8/1999 | Patterson et al. | |
| 5,972,913 A | 10/1999 | Yates | |
| 6,375,635 B1 | 4/2002 | Moutafis et al. | |
| 6,451,017 B1 | 4/2002 | Moutafis et al. | |
| 6,511,493 B1 | 1/2003 | Moutafis et al. | |
| 6,610,079 B1* | 8/2003 | Li | A61B 17/00491 606/213 |
| 6,884,247 B1 | 4/2005 | Hagan et al. | |
| 6,960,182 B2 | 11/2005 | Moutafis et al. | |
| 7,122,017 B2 | 10/2006 | Moutafis et al. | |
| 7,144,414 B2 | 12/2006 | Harvie et al. | |
| 7,785,347 B2 | 8/2010 | Harvie et al. | |
| 8,163,031 B2 | 4/2012 | Truckai et al. | |
| 8,313,492 B2 | 11/2012 | Wong et al. | |
| 8,357,169 B2 | 1/2013 | Henniges et al. | |
| 8,791,172 B2 | 7/2014 | Vogt et al. | |
| 8,951,265 B2 | 2/2015 | Schwappach | |
| 9,132,016 B2 | 9/2015 | Flaherty et al. | |
| 9,386,976 B2 | 7/2016 | Mayer et al. | |
| 10,433,921 B2* | 10/2019 | Librot | A61B 34/30 |
| 10,596,069 B2* | 3/2020 | Goodman | B01F 5/0695 |
| 2002/0045950 A1 | 4/2002 | Draenert | |
| 2002/0176788 A1 | 11/2002 | Moutafis et al. | |
| 2003/0125660 A1 | 7/2003 | Moutafis et al. | |
| 2004/0228736 A1 | 11/2004 | Moutafis et al. | |
| 2004/0243157 A1 | 12/2004 | Connor et al. | |
| 2006/0229550 A1 | 10/2006 | Staid et al. | |
| 2006/0264808 A1 | 11/2006 | Staid et al. | |
| 2007/0093899 A1 | 4/2007 | Dutoit et al. | |
| 2008/0269761 A1* | 10/2008 | Truckai | A61B 17/8805 606/94 |
| 2009/0062871 A1 | 3/2009 | Chin et al. | |
| 2010/0082072 A1 | 4/2010 | Sybert et al. | |
| 2012/0041444 A1 | 2/2012 | Einhorn | |
| 2012/0165940 A1 | 6/2012 | Sennett et al. | |
| 2013/0035561 A1* | 2/2013 | Sharkey | A61B 17/8811 600/301 |
| 2013/0046351 A1 | 2/2013 | Schwappach | |
| 2013/0110115 A1 | 5/2013 | Lackman | |
| 2013/0144249 A1 | 6/2013 | Fenton et al. | |
| 2013/0144348 A1 | 6/2013 | Schwappach | |
| 2014/0127301 A1 | 5/2014 | Alexis et al. | |
| 2014/0163567 A1* | 6/2014 | Lin | A61B 17/8836 606/94 |
| 2014/0194887 A1* | 7/2014 | Shenoy | A61B 17/8811 606/94 |
| 2015/0250598 A1 | 9/2015 | Yakimicki et al. | |
| 2015/0335370 A1 | 11/2015 | Sahatjian et al. | |
| 2016/0278835 A1* | 9/2016 | Liang | A61B 17/8819 |
| 2016/0303278 A1 | 10/2016 | Stein et al. | |
| 2017/0100507 A1* | 4/2017 | Angle | A61L 27/427 |

OTHER PUBLICATIONS

Serhan ER, Mehmet et al., Suture anchor fixation strength with or without augmentation in osteopenic and severely osteoporotic bones in rotator cuff repair: a biomechanical study on polyurethane foam model, J Orthop Surg Res., vol. 9, pp. 48-54.

Shridhar, Puneeth et al., A Review of PMMA Bone Cement and Intra-Cardiac Embolism, Materials, vol. 9, No. 10, pp. 821-834.

Steiner, C. et al., HCUP Projections: Mobility/Orthopedic Procedures 2003 to 2012, U.S. Agency for Healthcare Research and Quality, 2012.

* cited by examiner

METHOD AND INJECTION SYSTEM FOR BONE TISSUE IMPLANT

REFERENCE TO PENDING PRIOR PATENT APPLICATION

This patent application claims benefit of prior U.S. Provisional Patent Application Ser. No. 62/595,615, filed Dec. 7, 2017 by Paul V. Fenton Jr. et al. for METHOD AND INJECTION SYSTEM FOR BONE TISSUE IMPLANT, which patent application is hereby incorporated herein by reference.

FIELD OF THE INVENTION

The present invention relates to a method and injection system for embedding an implant in the bone tissue of a patient or other structure, and, more particularly, to a method and injection system to embed a flowable implant material into a porous region to form, shape and create the implant in situ where desired.

BACKGROUND OF THE INVENTION

At the present, bone anchor implants are used in patients for the attachment of soft tissue to the bone of a patient. Current anchors are generally implants made from prefabricated metallic, polymeric or synthetic materials, and are relatively rigid and manufactured in precise fixed shapes (i.e., fixed volume envelopes and fixed surface topologies).

Typically, anchors are screws or interference fit devices which are surgically embedded in the bone, beneath the cortical bone layer, and may have an eyelet for attaching sutures used to encircle soft tissue to affix the soft tissue to the bone.

To accommodate individual patient anatomical differences, it would be advantageous to have a polymeric implant, injection system and method to introduce the implant material in situ, allowing the polymeric material to be infused into the surrounding bone material and subsequently becoming solidified, rigid and secured at or proximate to the location where the implant is desired.

In addition to the attachment of soft tissue to the bone of a patient, it would also be advantageous if the polymeric material implant could be used to fill a void with relatively arbitrary shape or size in bony structures.

SUMMARY OF THE INVENTION

Accordingly, the present invention relates to a polymeric implant material, a method and an injection system to embed the implant material within a structure, such as a bone of a patient.

The present invention will be described with respect to a living patient and wherein the implant material is melted in order to fill a void in a bone of a patient, or to create an anchor within the bone of a patient, however, it will be seen that the present invention can also be used with other structures, not involving a living patient. By patient, it is meant that the present invention is applicable to any mammal.

A polymeric material that can be used with an exemplary embodiment is a low flowing point material such as polycaprolactone [PCL] with a flowing temperature of about 60 degrees Centigrade. With such material, the implant material can be melted so as to be infused into the desired area, such as the bone of a patient, without necrotic damage to that bone. Necrotic side effects occur in bone when the temperature is in excess of 57 degrees Centigrade for long durations of time and can be mitigated if the duration of temperature exposure in excess of 60 or 70 or 80 degrees Centigrade is shortened by the cooling effect of the heat transfer from the polymeric material to the body. Cooling to below 60 degrees Centigrade solidifies the polymeric material, secures it to the bone in situ, and provides the anchoring function of currently available implants or the filling of a void in bone.

The resultant implant is shaped to fit the underlying bone structure whereas the shape of current anchors are predetermined and forces the underlying bone structure to conform to the manufactured shape of current anchors. Other polymeric materials have lower temperature flowing points which would be preferred but are not yet biocompatible but may be in the future.

The implant injection system includes a handle with a shaft extending outwardly therefrom, and a means to heat the implant material so as to melt that material and allow it to be infused into the desired area. The actual heating of the material from its normal solid state to its flowable state can take place in situ within the body or other structure, or ex vivo, that is, just outside the body or structure and proximate to the desired location of the implant. The transformation of the material within the body from a solid state into a flowable state such as by heating can be accomplished with an active heating element within the injection system shaft. The ex vivo heating of the material can be accomplished with the shaft body of the injection system being actively heated so as to melt the material followed by a short time duration transfer of the melted material by the injection system to the implantation site for the material to be infused before the material re-solidifies and becomes rigid.

Accordingly, in one exemplary embodiment, the distal end of the shaft includes an electrical resistance heater that is used to heat and melt the implant material so as to render that implant material flowable. Alternatively, the heating may be applied to the implant material by means of a heated fluid, such as hot water, heated air or some other external heating system that heats and melts the implant material so as to render it flowable. As such, the distal end of the injection system can be placed into or proximate to the cancellous bone where the implant is desired, whereupon the implant material can be transformed into a flowable state and caused to migrate into the cancellous bone to create a bone anchor or to fill a void.

In another exemplary embodiment, there can be a looped suture that passes though the implant material, with the free ends of the looped suture extending outwardly from the implant material. As such, the implant material, when infused into the cancellous bone, anchors the suture loop to the bone and the free ends of the suture can surround the soft tissue and be tied together so as to affix that soft tissue to the bone.

In a still further exemplary embodiment, the implant material can be formed of multiple layers, with an inner layer or layers (or region or regions) that has/have a known flowing temperature and with an outer layer or layers (or region or regions) flowing at a higher temperature. With this construction, the heater is designed to reach the flowing temperature of the inner layer or layers (or region or regions) but not reach the flowing temperature of the outer layer or layers (or region or regions) so that only the inner layer or layers (or region or regions) is/are melted and diffused into the cancellous bone.

In another exemplary embodiment, another means of producing an anchor or filler that fills a void is to use an epoxy two-part polymer cement like polymethyl methacrylate (PMMA), which is loaded by means of a cement loading syringe into the distal end of an injection system. The implant material is then inserted by the injection system into the desired site. The PMMA material is specifically located at the distal end of the injection system since PMMA is rheopectic and hence difficult to flow down the length of a shaft.

More particularly, a material that is rheopectic exhibits a time-dependent increase in viscosity—the longer the fluid undergoes shearing force, the higher its viscosity. Thus PMMA, which is rheopectic, is difficult to flow down the length of a shaft. Accordingly, rather than trying to push the rheopectic PMMA material down the barrel of the implant device, the PMMA material is initially located at the distal end of the syringe, thereby eliminating the need to flow the PMMA material down the length of a shaft.

In one preferred form of the invention, there is provided an implant injection system for implanting an implant material into a structure comprised of a latticework having spaces formed therein, the implant injection system containing a quantity of a meltable implant material, and a heater for heating the meltable implant material to form a flowable implant material for introduction into the spaces of the latticework.

In another preferred form of the invention, there is provided a method for implanting an implant material into a structure comprising a latticework having spaces formed therein, the method comprising the steps of:
  providing an implant injection system having a quantity of a meltable implant material located within the implant injection system;
  heating the meltable implant material to create a flowable implant material; and
  introducing the flowable implant material into the spaces of the latticework to harden in situ.

In another preferred form of the invention, there is provided a method for affixing soft tissue to the bone of a patient, the method comprising the steps of:
  providing an implant injection system containing a quantity of a meltable implant material with a suture looped through the quantity of the meltable implant material and with free ends of the suture extending outwardly therefrom;
  heating the quantity of meltable implant material to melt the meltable implant material to form a flowable implant material;
  flowing the flowable implant material into the bone of a patient;
  providing a quantity of soft tissue; and
  tying the free ends of the suture around the soft tissue to affix the soft tissue to the bone of a patient.

In another preferred form of the invention, there is provided a method for affixing soft tissue to the cancellous bone of a patient, the method comprising the steps of:
  providing an implant injection system having a distal end, a heater located proximate to the distal end of the implant injection system, and a quantity of bone implant material located proximate to the distal end of the implant injection system, the quantity of bone implant material comprising multiple regions of bone implant material, with an inner region having a predetermined flowing point temperature and outer regions having a flowing point temperature higher than the flowing point temperature of the inner region;
  positioning the distal end of the implant injection system within the cancellous bone of a patient; and
  activating the heater to create a temperature sufficient to melt the bone implant material of the inner region but lower than the flowing temperature of the outer regions to allow the bone implant material of the inner region to flow into the cancellous bone of the patient.

In another preferred form of the invention, there is provided an implant injection system for inserting a flowable material into a bone of a patient, the implant injection system comprising:
  a container having a distal end and an open proximal end, a plunger movable with the container, a heater located proximate to the distal end of the container; and
  a quantity of meltable material within the container and located proximate to the heater, wherein the material may be melted by the heater and forced from the distal end of the container by movement of the plunger.

In another preferred form of the invention, there is provided a method for loading a bone cement material into a delivery tip of an implant injection system, the method comprising the steps of:
  providing a cement loading syringe having a barrel with an open distal end, a plunger and a quantity of bone cement material located at the open distal end of the barrel;
  placing the open distal end of the barrel of the cement loading syringe proximate to the delivery tip of the implant injection system; and
  activating the plunger of the cement loading syringe to force the bone cement material from the cement loading syringe into the delivery tip of the implant injection system.

These and other features and advantages of the present invention will become more readily apparent during the following detailed description of the preferred embodiments of the invention, which is to be taken in conjunction with the drawings herein.

DETAILED DESCRIPTION OF THE PREFERRED EMBODIMENTS

Figure 1A:
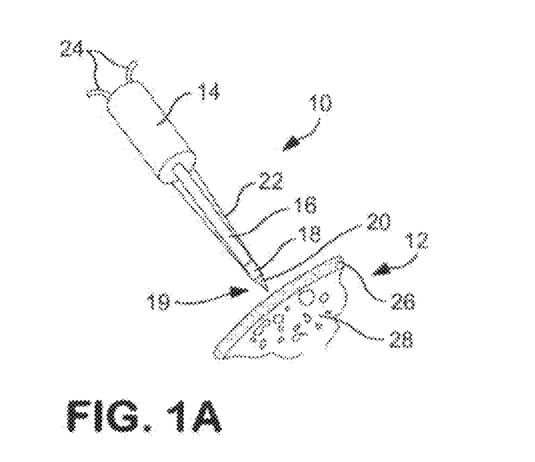
FIGS. 1A-1C are schematic views illustrating an implant injection system formed in accordance with the present invention and showing a method for implanting implant material into the cancellous bone tissue of a patient.
Figure 1B:
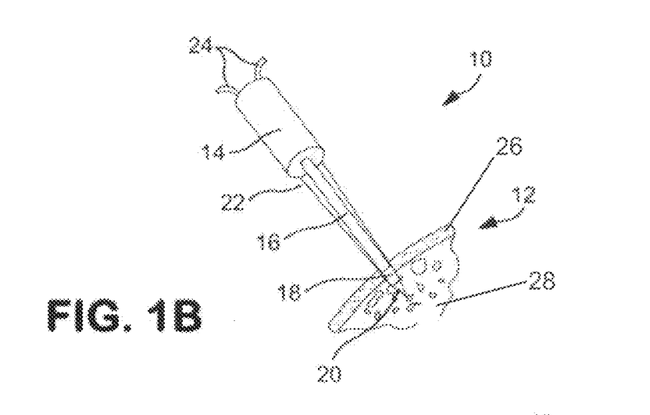
Figure 1C:
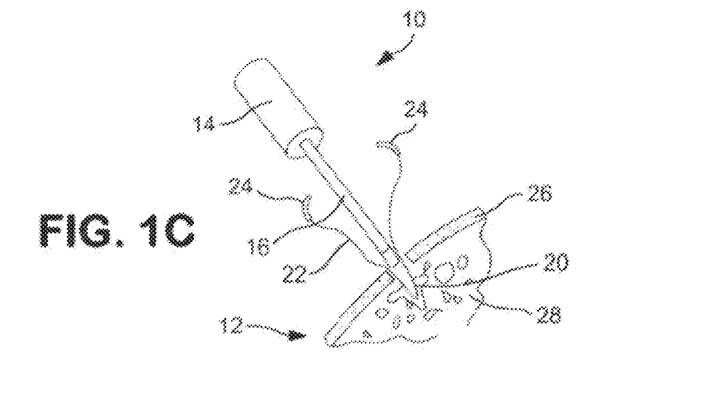

Referring now to FIGS. 1A-1C, there is shown schematic views illustrating an implant injection system 10 formed in accordance with the present invention and showing the steps taken to carry out a method of the present invention. As can be seen in FIG. 1A, the implant injection system 10 is positioned in close proximity to a bone 12 of a patient, and the implant injection system 10 includes a handle 14 and a shaft 16 extending therefrom. In this exemplary embodiment, a small resistance heater 18 is located at the distal end of the shaft 16.

Bone implant material 20 is positioned at the distal end of the implant injection system 10 and a suture 22 is looped through that bone implant material 20 and the free ends 24 of the suture 22 extend from that bone implant material 20 proximally towards the handle 14.

Moving on to the step shown in FIG. 1B, the shaft 16 has pierced the cortical bone layer 26 of the bone 12 and the distal end of the shaft 16 is located in the cancellous bone 28.

In the step of FIG. 1C, the implant injection system 10 has been withdrawn from the bone 12 of the patient and the bone implant material 20 separated therefrom such that the bone implant material 20 remains in the cancellous bone 28. To reach the step of FIG. 1C, the bone implant material 20 has been heated by the resistance heater 18 to melt the bone implant material 20 and allow the implant injection system 10 to be pulled clear of the bone implant material 20. The bone implant material 20 itself has melted and spread through the interstices of the cancellous bone 28 so that the bone implant material 20 is firmly affixed to the cancellous bone 28, with the free ends 24 of the suture 22 available for use in securing soft tissue to the cortical bone layer 26.

It should be appreciated that in one form of the invention, the bone implant material 20 is secured to the distal end of shaft 16, adjacent to the resistance heater 18 disposed at the distal end of shaft 16, so that bone implant material 20 essentially forms, in its pre-heated state, the distal end of shaft 16; and so that bone implant material 20 is carried into cancellous bone 28 by shaft 16, whereupon activation of resistance heater 18 causes bone implant material 20 to flow off the distal end of shaft 16 and into the interstices of cancellous bone 28. Thus, in one form of the invention, the heated bone implant material 20 is set at the distal end of shaft 16 and, when heated by resistance heater 18, simply flows off the shaft and into the interstices of the cancellous bone 28, whereafter it sets when cooled to body temperature. In another form of the invention, the bone implant material 20 may be positioned within a syringe chamber (not shown) disposed at the distal end of shaft 16, and the heated bone implant material may be ejected, under force, out of the syringe chamber and into the interstices of cancellous bone 28, whereafter it will set when cooled to body temperature.

In the method shown in FIGS. 1A-1C, the heater 18 has been described in the exemplary embodiment to be an electrical resistance heater, however, it may be seen that other types of heaters can be used instead of a resistance heater in any of the embodiments described herein, including a heater employing a heated fluid, such as heated water or heated air.

In addition, in this embodiment and in subsequent applicable embodiments, the meltable implant material is one having a low flowing temperature such as polycaprolactone (PCL) which has a flowing point of about 60 degrees Centigrade so that necrotic damage to the bone is prevented. When that material is thereafter cooled, it hardens within the bone at the desired location and becomes an effective anchor for a suture or fills a void in the bone.

Accordingly, as an alternative to the use of a resistance heater, the implant bone material 20, located in one embodiment at the distal end of an implant instrument, can be placed into a heated chamber or bath so that the implant bone material softens to a moldable state and then can be emplaced into the cancellous bone.

Turning now to FIGS. 2A-2E, there is shown a series of steps further illustrating the use of the present implant injection system 10 in carrying out the present method of emplacing the bone implant material 20. As can be seen, in the step of FIG. 2A, a hole 30 has been made in the bone 12 of the patient that passes through the cortical bone layer 26 and extends into the cancellous bone 28. As with the embodiment of FIGS. 1A-1C, at the end of the shaft 16, there is affixed the bone implant material 20 and which has the suture 22 passing through the bone implant material 20, with the free ends 24 of the suture 22 extending outwardly therefrom. The resistance heater 18 is also located at the distal end of the shaft 16 so that the resistance heater 18 can heat the bone implant material 20 to its melt point to cause it to be flowable.

Figures 2A, 2B:
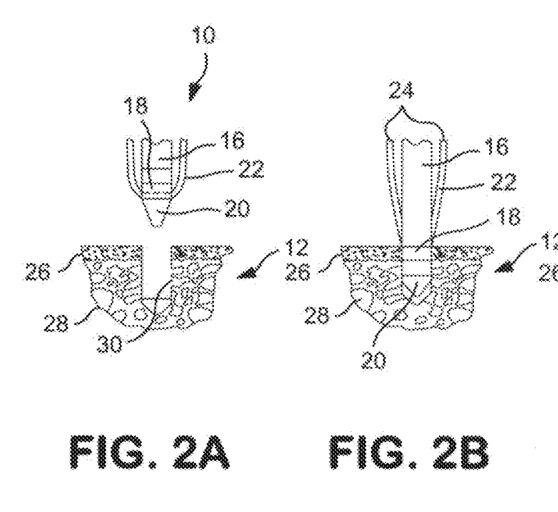
FIGS. 2A-2E are further schematic views illustrating the distal end of the implant injection system of FIGS. 1A-1C and showing the method of implanting implant material into the cancellous bone tissue of a patient.

In the step of FIG. 2B, the distal end of the shaft 16 has been introduced into the hole 30 so that the bone implant material 20 passes through the cortical bone layer 26 and into the cancellous bone 28.

Figure 2C:
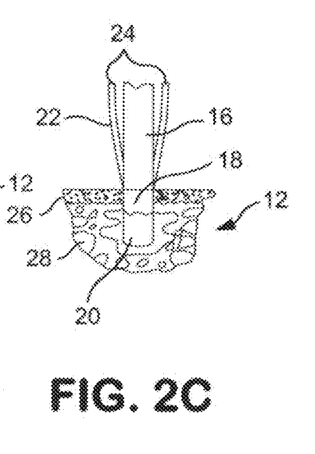
Figure 2D:
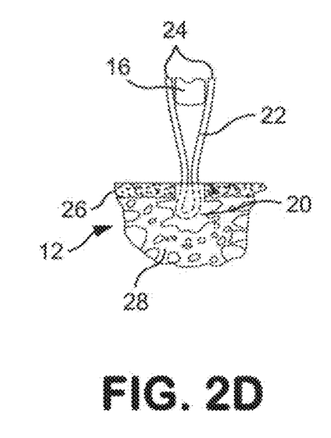

In the step of FIG. 2C, the resistance heater 18 has been activated and the bone implant material 20 has melted and spread into the cancellous bone 28, thereby forming a mass having a larger diameter than the diameter of the hole 30. In the step of FIG. 2D, the shaft 16 has been retracted, leaving the melted bone implant material 20 to re-solidify at body temperature within the cancellous bone 28, with the suture 22 passing through the bone implant material 20 so that the suture 22 is anchored within the bone 12.

Figure 2E:
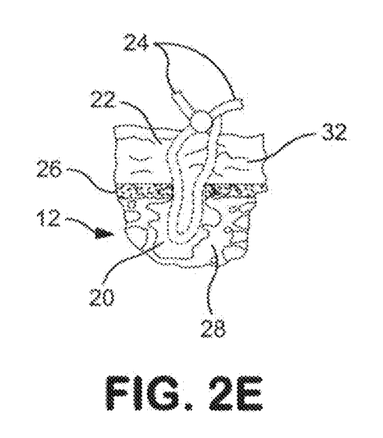

Finally, in the step of FIG. 2E, there can be seen the re-hardened bone implant material 20 positioned within the cancellous bone 28, with the free ends 24 of the suture 22 tied together, encircling soft tissue 32, so that the soft tissue 32 is affixed to the cortical bone layer 26.

Figures 3A, 3B:
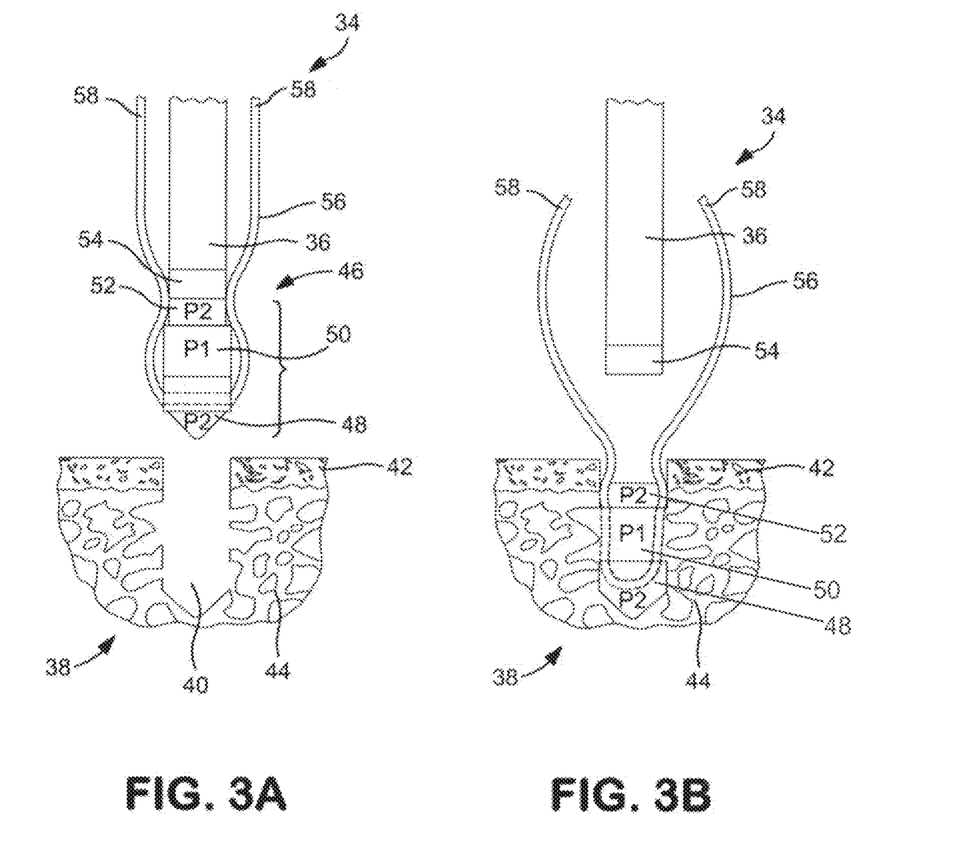
FIGS. 3A and 3B are schematic views showing an alternative exemplary embodiment of an implant injection system formed in accordance with the present invention and showing a method of use for implanting an implant material into the cancellous bone tissue of a patient.

Turning next to FIGS. 3A and 3B, there is shown steps of an alternative embodiment of an implant injection system 34 of the present invention, wherein the distal end of the shaft 36 is in position proximate to the bone 38 of the patient. In this embodiment, again a hole 40 has been drilled in the bone 38 and passes through the cortical bone layer 42 and enters into the cancellous bone 44.

In this exemplary embodiment, however, at the distal end of the shaft 36 there is a multi-layer bone implant material 46. As can be seen in FIGS. 3A and 3B, the bone implant material 46 comprises a distal region 48, an intermediate region 50 and a proximal region 52. The distal region 48 and proximal region 52 comprise a high melt temperature polymer while the intermediate region 50 comprises a lower melt temperature polymer. In the exemplary embodiment, the polymer used in the distal region 48 and the proximal region 52 can be the same material.

Again, a resistance heater 54 is provided to carry out the melt step of the present invention. The suture 56 passes through the distal region 48 of the bone implant material and has its free ends 58 external of the bone 38 of the patient.

As such, turning now to FIG. 3B, again, as described with respect to FIGS. 1A-1C and 2A-2E, the resistance heater 54 has heated the bone implant material 46 and has been retracted from the cortical bone layer 42, leaving the bone implant material 46 in the cancellous bone 44 of the patient.

In this embodiment, however, the intermediate region 50, being formed out of a polymer having a lower melt temperature than the polymers of the distal region 48 and the proximal region 52, has melted and infused into the cancellous bone 44 of the patient. The polymer or polymers of the distal region 48 and proximal region 52, being of a higher melt point, have not melted and remain intact in situ within the cancellous bone 44 of the patient.

In this form of the invention, proximal region 52 can make a simple friction fit with the distal end of shaft 16, such that bone implant material 46 can disconnect from the distal end of shaft 16 after bone implant material 46 has been positioned within bone 38.

The suture 56 is firmly anchored to the distal region 48 and has its free ends 58 extending outwardly from the bone 38 of the patient for attachment of an object (such as soft tissue) to the bone 38 of the patient.

Alternatively, if desired, proximal region 52 of bone implant material 46 may be omitted and intermediate region 50 may be connected to the distal end of shaft 16, whereupon bone implant material 46 will detach from the shaft when the bone implant material is heated to a flowable state.

Figure 4:
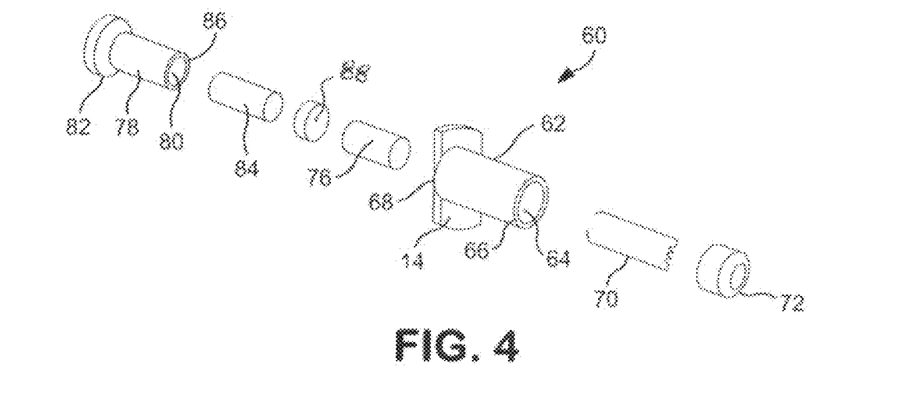
FIG. 4 is an exploded schematic view of another implant injection system of the present invention that can be used to melt and introduce a polymer into the bone of a patient.

Turning now to FIG. 4, there is shown an exploded, schematic view of a still further implant injection system 60 of the present invention that can be used to melt and introduce a polymer bone implant material into the bone of a patient. As can be seen in FIG. 4, the implant injection system 60 comprises an insulated container 62 having a cylindrical opening 64 extending therethrough, and the implant injection system 60 has a distal end 66 and a proximal end 68. A heater 70 is provided proximate the distal end 66 of the container 62 and, in the exemplary embodiment, the heater 70 may be an electrical resistor. A nozzle 72 is also located at the distal end 66 of the container 62 (and the implant injection system 60 itself). A flange 74 is provided at the proximal end 68 of the container 62 and the purpose of the flange 74 will be later explained.

Within the cylindrical opening 64 of container 62, there is located a meltable polymer capsule (which may also be referred to as a cartridge or block or plug, etc.) 76. A plunger 78 interfits into the cylindrical opening 64 and is axially movable within the cylindrical opening 64. The plunger 78 also has a recessed opening 80 and a closed proximal end flange 82, and a battery 84 is interfitted into the recessed opening 80 that is used to power the heater 70. At the distal end 86 of the plunger 78, there is provided an insulator 88 that closes the distal end 86 of the plunger 78 and can serve to retain and insulate the battery 84 within the recessed opening 80 of the plunger 78.

As is conventional, there is suitable wiring to electrically connect the battery 84 to the heater 70 and a switch, not shown, that can be used to complete the circuit between the battery 84 and the heater 70 to activate the heater 70 at the will of the user. Typical switches that can be used include manual switches or pressure-actuated switches that complete the electrical circuit when the plunger 78 is pushed inwardly toward the distal end 66 of the container 62.

Figure 5:
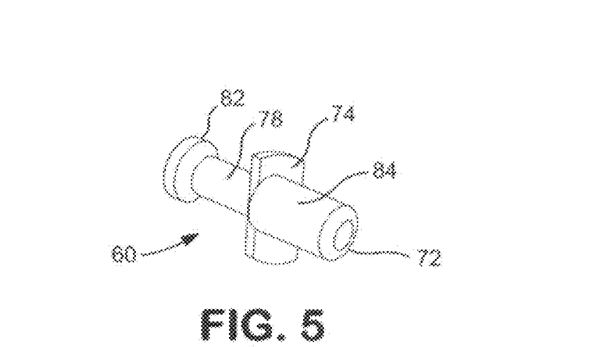
FIG. 5 is a perspective view of the assembled implant injection system of FIG. 4.

In FIG. 5, there is a perspective view of the complete implant injection system 60 assembled from the components of FIG. 4. Accordingly, the user can hold the implant injection system 60 by holding the flange 74 and then depressing the plunger 78 inwardly to operate the implant injection system 60.

Figure 6:
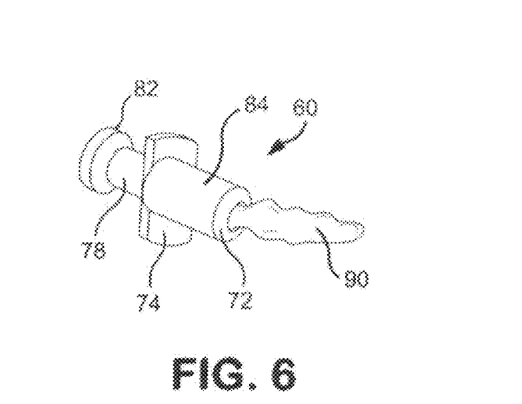
FIG. 6 is a perspective view of the implant injection system of FIG. 4 and illustrating its use in injecting a flowable melted polymer material into the bone of a patient.

In FIG. 6, taken along with FIGS. 4 and 5, it can be seen that the polymer capsule 76 of FIG. 4 has been melted by the activated heater 70 such that the polymer emerges as a flowable, melted polymer material 90 out of the nozzle 72 that may be used to form an anchor in, and/or to fill a void in, a bony structure.

Note that with the construction of FIGS. 4-6, the polymer is melted by heater 70 at the distal end of implant injection system 60, adjacent to exit nozzle 72. Thus, the melted polymer only needs to travel a short distance to its implant site, whereupon it re-hardens within the bone.

Figure 7A:
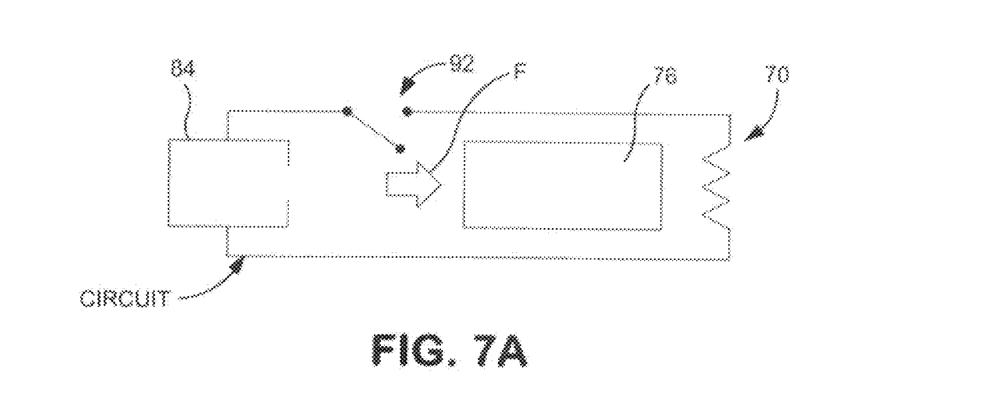
FIGS. 7A and 7B are schematic views of an electrical circuit usable with the embodiment of FIG. 4.
Figure 7B:
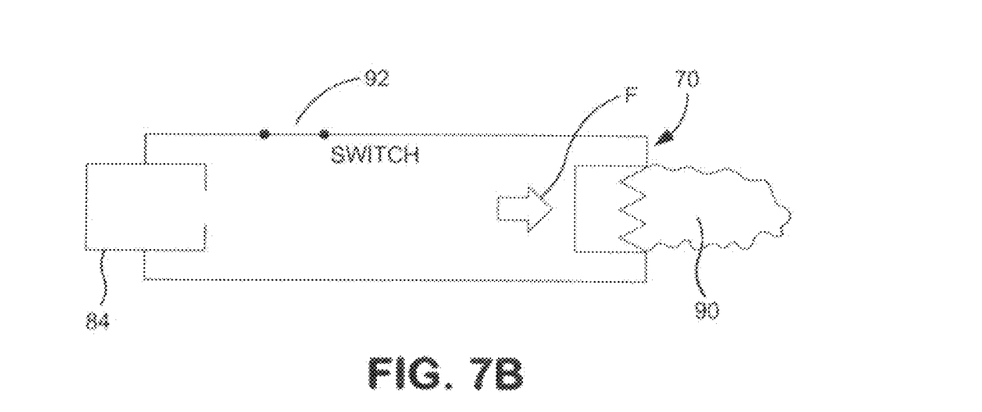

Turning next to FIGS. 7A and 7B, there is shown a schematic view of a typical electrical circuit that can be used with the embodiment of FIG. 4. In FIG. 7A, the circuit is open since the manual switch 92 is in its open position. As such, the battery 84 is not connected to the heater 70 so the polymer capsule 76 remains intact (i.e., in solid form). An arrow F indicates the force exerted on the polymer capsule 76 as the plunger 78 (FIG. 4) is pushed forward by the user.

In FIG. 7B, the circuit has been closed since the manual switch 92 has been moved to its closed position and therefore the electrical energy of the battery 84 passes to the heater 70 that heats the polymer to a temperature exceeding its flowing temperature. The force F can now be exerted on the plunger 78 (FIG. 4) and the flowable, melted polymer 90 emerges from the implant device 60 (for subsequent re-hardening at the implant site).

Figure 8A:
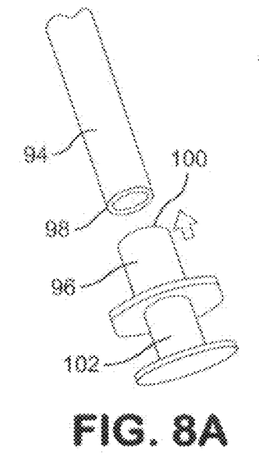
FIGS. 8A-8G are schematic views illustrating a method of loading an applicator tip with a material, such as a bone cement, to ready the applicator for injecting the material into the bone of a patient.

Next, with reference to FIGS. 8A-8G, there are shown schematic views illustrating a method of filling an implant injection system 94 with polymethyl methacrylate (PMMA) bone cement. As can be seen in FIG. 8A, a cement loading syringe 96 is shown in position proximate to the delivery tip 98 of the implant injection system 94. The cement loading syringe 96 contains a predetermined quantity of a bone cement, such as PMMA (not shown), therein and the cement loading syringe 96 has an open, distal end 100 and a movable plunger 102 at the opposite end thereof.

Figures 8B, 8C, 8D:
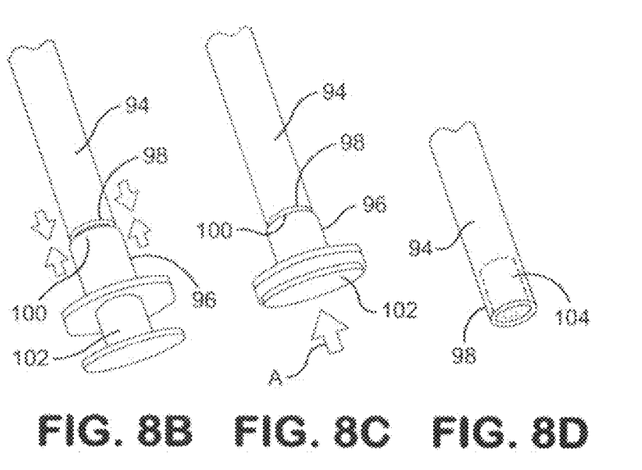

In FIG. 8B, the cement loading syringe 96 is in position proximate to the delivery tip 98 of the implant injection system 94. In FIG. 8C, the movable plunger 102 has been depressed to load the PMMA into the delivery tip 98 of the implant injection system 94. As such, in FIG. 8D, the cement loading syringe of FIG. 8C has been removed and a PMMA bolus 104 is present in the open, delivery tip 98 of the implant injection system 94, ready for injection into the bone of a patient.

The PMMA material is specifically located at the distal end of the syringe 96 since PMMA is rheopectic and is difficult to push down a tube. A rheopectic material has a fluid flow behavior wherein time and stress affect the viscosity—the longer a rheopectic material undergoes a shearing force, the higher its viscosity and the lower its flowability. Accordingly, rather than trying to push the material down the full length of the barrel of the syringe, the PMMA material is positioned at the distal end of the implant injection system 94, which then requires a short travel to the implant site.

Figure 8E:
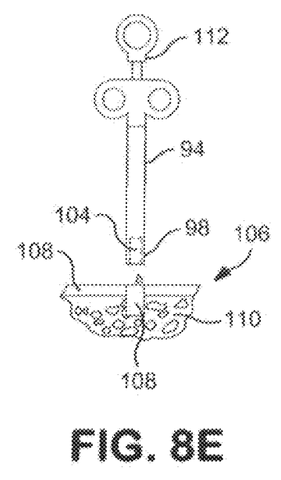
Figure 8F:
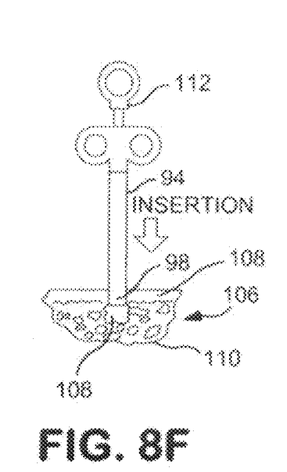
Figure 8G:
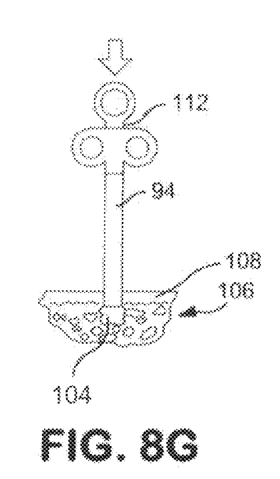

Turning next to FIG. 8E, the implant injection system 94 is shown in position to deliver the PMMA into the bone 106 of a patient. As can be seen in FIG. 8E, a hole 108 has been drilled into the bone 106 that passes through the cortical bone layer 108 and into the cancellous bone 110. The implant injection system 94 is shown in FIGS. 8E-8G to be a syringe with a plunger 112. Next, in FIG. 8F, the delivery tip 98 of the implant injection system 94 is placed into the hole 108 and is positioned proximate to the cancellous bone 110.

Finally, in FIG. 8G, the plunger 112 has been depressed so as to force the PMMA bolus 104 into the cancellous bone 110, where it is allowed to expand into the cancellous bone 110 to act as an anchor or reinforcement.

A suture could also be added to this embodiment to retain soft tissue to a bone surface.

Figure 8H:
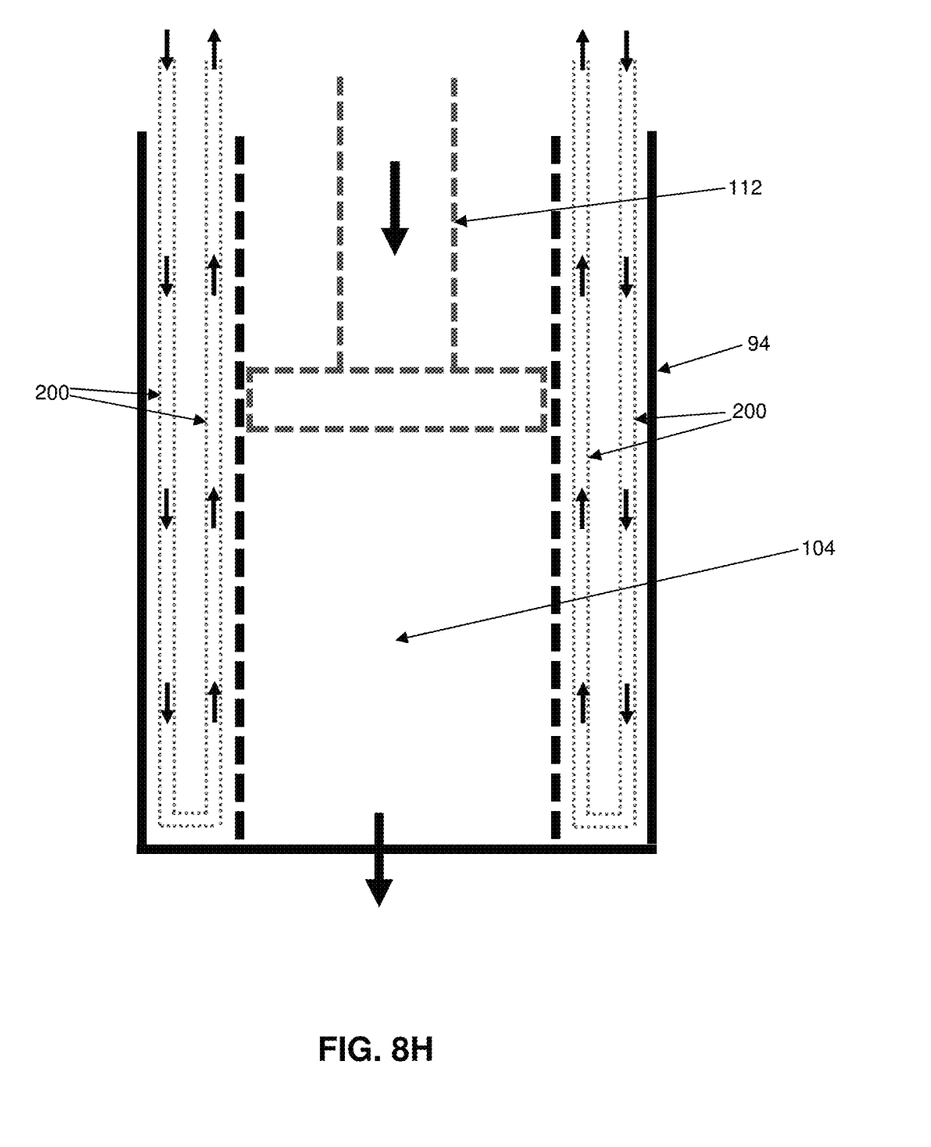
FIG. 8H is a schematic view showing an additional construction formed in accordance with the present invention.

Furthermore, if desired, cooling can be provided to the distal end of implant injection system 94 to retard polymerization of the PMMA cement and allow for improved flowability and increased working time. By way of example but not limitation, implant injection system 94 may be configured to circulate a cooling fluid through the distal end of implant injection system 94 so as to provide cooling to PMMA bolus 104 prior to the injection of the PMMA bolus into cancellous bone 110. See, for example, FIG. 8H, which shows passageways 200 for circulating a cooling fluid through the distal end of implant injection system 94 so as to provide cooling to PMMA bolus 104 prior to the injection of the PMMA bolus into cancellous bone 110.

Modifications of the Preferred Embodiments

While the present invention has been set forth in terms of a specific embodiment or embodiments, it will be understood that the present implant device and the method of using the same herein disclosed may be modified or altered by those skilled in the art to other configurations. Accordingly, the invention is to be broadly construed and limited only by the scope and spirit of the claims appended hereto.

The invention claimed is:

1. An implant injection system for implanting an implant material into bone, the implant injection system comprising:
   a shaft having a distal end and a proximal end;
   an implant material having a non-flowable state and a flowable state, wherein the implant material forms the distal end of the shaft when the implant material is in the non-flowable state;
   a suture extending through the implant material when the implant material is in the non-flowable state; and
   a heater disposed proximate to the implant material for heating the implant material to its flowable state, whereby the implant material separates from the distal end of the shaft and flows into the bone.

2. The implant injection system of claim 1 wherein the bone is a bone of a mammal.

3. The implant injection system of claim 1 wherein the heater is an electrical resistance heater.

4. The implant injection system of claim 3 wherein the implant injection system further comprises a source of electricity for activating the electrical resistance heater.

5. The implant injection system of claim 4 wherein the source of electricity is a battery located within the shaft.

6. The implant injection system of claim 1 wherein the heater employs a quantity of heated fluid.

7. The implant injection system of claim 6 wherein the heated fluid is heated water.

8. The implant injection system of claim 6 wherein the heated fluid is heated air.

9. The implant injection system of claim 1 wherein the implant material has a flowing temperature of about 60 degrees Centigrade.

10. The implant injection system of claim 1 wherein the implant material is polycaprolactone.

11. The implant injection system of claim 1 wherein the implant material is a polymer.

12. The implant injection system of claim 1 wherein the suture comprises a distal portion and a proximal portion, wherein the distal portion of the suture is passed through the implant material and the proximal portion of the suture comprises two free ends of suture.

13. The implant injection system of claim 12 wherein the two free ends of suture are configured to attach soft tissue to bone.

* * * * *